United States Patent
García Cano et al.

(10) Patent No.: US 11,981,878 B2
(45) Date of Patent: May 14, 2024

(54) METHOD FOR MUNICIPAL SOLID WASTE RECLAMATION

(71) Applicant: ECONWARD TECH., Madrid (ES)

(72) Inventors: Rubén García Cano, Madrid (ES); Jorge Crespo Lobo, Madrid (ES); Ángel Rumbero Sanchez, Madrid (ES); Nuria Cano Adamuz, Madrid (ES); Alejandro Villacampa Sanagustín, Madrid (ES); Oscar Orozco González, Madrid (ES)

(73) Assignee: ECONWARD TECH., Madrid (ES)

( * ) Notice: Subject to any disclaimer, the term of this patent is extended or adjusted under 35 U.S.C. 154(b) by 79 days.

(21) Appl. No.: 17/621,028

(22) PCT Filed: Jun. 21, 2019

(86) PCT No.: PCT/ES2019/070436
§ 371 (c)(1),
(2) Date: Dec. 20, 2021

(87) PCT Pub. No.: WO2020/254699
PCT Pub. Date: Dec. 24, 2020

(65) Prior Publication Data
US 2022/0364017 A1    Nov. 17, 2022

(51) Int. Cl.
*C11B 13/00* (2006.01)
*B03B 9/06* (2006.01)
(Continued)

(52) U.S. Cl.
CPC ............... *C11B 13/00* (2013.01); *B03B 9/06* (2013.01); *B09B 3/00* (2013.01); *C07C 51/42* (2013.01);
(Continued)

(58) Field of Classification Search
CPC ......... C11B 13/00; C07C 51/42; C07C 51/47; C07C 51/487; C11C 1/08; C11C 1/10; B03B 9/06; B09B 3/00
See application file for complete search history.

(56) References Cited

U.S. PATENT DOCUMENTS

| | | | |
|---|---|---|---|
| 4,797,135 A * | 1/1989 | Kubat | C10L 5/44 44/589 |
| 7,985,577 B2 * | 7/2011 | Choate | C12M 23/02 435/801 |

(Continued)

FOREIGN PATENT DOCUMENTS

| | | | | |
|---|---|---|---|---|
| CN | 108580520 | * | 9/2018 | ............... B09B 3/00 |
| CN | 108580520 A | | 9/2018 | |

(Continued)

OTHER PUBLICATIONS

CN108580520, Liu Jianwei et al., Small and medium-size city household garbage sorting treatment system and method, English Translation, pp. 1-24 (Year: 2018).*

*Primary Examiner* — Yate' K Cutliff
(74) *Attorney, Agent, or Firm* — Hayes Soloway P.C.

(57) ABSTRACT

The present invention relates to a method for municipal solid waste (MSW) reclamation in a continuous or discontinuous process first for converting said waste into organic biomass and subsequently extracting and recovering the most chemical compounds contained in said biomass possible, such as triglycerides, sugars and proteins. Therefore, the invention is comprised in the field of recycling, transforming solid waste into reusable solids and biofuels.

19 Claims, 4 Drawing Sheets

(51) Int. Cl.
  *B09B 3/00*   (2022.01)
  *C07C 51/42*  (2006.01)
  *C07C 51/47*  (2006.01)
  *C07C 51/487* (2006.01)
  *C11C 1/08*  (2006.01)
  *C11C 1/10*  (2006.01)
  *C12P 5/02*  (2006.01)

(52) U.S. Cl.
  CPC ............ *C07C 51/47* (2013.01); *C07C 51/487* (2013.01); *C11C 1/08* (2013.01); *C11C 1/10* (2013.01); *C12P 5/023* (2013.01)

(56) References Cited

U.S. PATENT DOCUMENTS

| | | | | |
|---|---|---|---|---|
| 9,545,650 | B2* | 1/2017 | Wang | C05F 17/00 |
| 2014/0315258 | A1* | 10/2014 | Nguyen | D21B 1/12 |
| | | | | 435/162 |

FOREIGN PATENT DOCUMENTS

| | | |
|---|---|---|
| WO | 03043939 A2 | 5/2003 |
| WO | 2018100544 A1 | 6/2018 |

* cited by examiner

METHOD FOR MUNICIPAL SOLID WASTE RECLAMATION

CROSS-REFERENCE TO RELATED APPLICATIONS AND PRIORITY

This patent application claims priority from PCT Application No. PCT/ES2019/070436 filed Jun. 21, 2019. This patent application is herein incorporated by reference in its entirety.

The present invention relates to a method for municipal solid waste (MSW) reclamation in a continuous or discontinuous process first for converting said waste into organic biomass and subsequently extracting and recovering the most chemical compounds contained in said biomass possible, such as triglycerides, sugars and proteins. Therefore, the invention is comprised in the field of recycling, transforming solid waste into reusable solids and biofuels.

STATE OF THE ART

Conventionally, MSW has been eliminated by dumping in landfills or by incineration. However, these methods for disposing of the waste product pollute the ground, the water and the air and require the use of land that could be used for other purposes.

MSW comprises significant amounts of recyclable material, including components such as cellular organic biowaste (such as food waste, garden waste, wood, paper and cardboard), plastic, glass, ferrous metals, and non-ferrous metals (such as aluminum). MSW sorting operations for recovering the different components are known in the art, but said known methods are typically inefficient. The biowaste fractions of the prior art are typically impure and contaminated with several components, such as enzyme hydrolysis and fermentation inhibitors, which usually render these cellulosic biowaste fractions unsuitable for being converted into monosaccharides and optional fermentation products at a commercially acceptable rate and yield. For this reason, MSW fractioning methods of the prior art generally recover value from organic biowaste by incineration (energy recovery), gasification (by pyrolysis), or composting.

These methods for municipal solid waste (MSW) treatment by pressurized steam have been an industrial reality for at least 120 years. The same can be said of the techniques of extraction by hydrolysis of byproducts and waste, which were developed before the Second World War.

Since then, the challenges and demands of MSW utilization are still essentially the same: sorting, hygiene and cost-effectiveness.

In this manner, for the purpose of improving these three points the concept of biomass biorefining is already becoming standardized by several technological companies, however, the concept of MSW biorefining is novel.

Having the capacity to extract molecules with a high added value from the organic fraction of municipal solid waste is an exceptional output. These molecules, moreover, could replace the molecules obtained by conventional methods, lowering costs, and most importantly, obtained from a raw material that, though not renewable, can be considered virtually infinite. Given that municipal waste generation is growing worldwide, although the trend is the reduction and the generation of technologies for recycling, minimizing said waste, the world population is growing, and developing countries, are generating an enormous amount of waste that needs to be recovered and utilized for different industries.

It is here where MSW biorefining plays a critical role in minimizing waste and utilizing it, thereby meeting recycling goals set by the European Union for Member States.

However, among the drawbacks in the art, the lack of research in this field and, furthermore, the high energy costs of extraction and the stigma created with respect to utilization of "garbage" must be mentioned.

Another drawback in the art is the lack of an ability to utilize 100% of said organic matter, despite the fact that it behaves like an excellent organic extract. This is due to operating costs for comprehensive utilization of said extract.

No one has obtained a comprehensive utilization of the different biomasses which currently exist, and much less MSW biomass, in a continuous manner in an industrial method. Despite the immense potential of this biomass, there is a void in the innovation and development of this type of biorefining.

Furthermore, there is another energy recovery from the organic fraction of the municipal solid waste, in this case by a biomethanation process, which consists of the decomposition of organic matter in the absence of oxygen to produce a methane-rich gas, biogas, obtaining as a byproduct a semi-liquid waste very rich in organic matter and nutrients, digestate. Usually the total solids content of the organic fraction of the municipal solid waste is high (greater than 15%), so a dry biomethanation process is performed. The biogas contains a specific heating capacity in the range of 15-25 kWh/Nm$^3$, depending on the composition of the organic fraction of the municipal solid waste. The biogas can be used for producing heat and/or electricity.

The biomethanation process begins with a step of pre-treatment, in which impurities (glass, inert materials, plastics) are removed for the purpose of obtaining an amount of foreign materials less than 10%. Subsequently, the material can be shredded for the purpose of homogenizing and reducing the particle size to values of 2-8 mm. Depending on the total solids content, the organic fraction is dissolved with water to reach a solids content within the range of dry anaerobic digestion (20-30% in total solids). The obtained organic fraction is used as feedstock (substrate) of the digester.

The problem associated with this method of reclamation is the presence of contaminants in the MSW which are introduced in digesters, causing bacterial growth and activity inhibition, as well as competition with other microorganisms also present in the MSW which are also introduced in the digester. Another drawback is the introduction of foreign materials in the feedstock (substrate). This causes problems associated with the build-up of foreign materials in the digester, which entails a high maintenance cost (the digester has to be shut down, the impurities removed, and started back up again).

DESCRIPTION OF THE INVENTION

The present invention relates to a continuous or discontinuous method of reclamation, first comprising a physical and chemical pre-treatment for the transformation of municipal solid waste (MSW) into organic biomass and a subsequent treatment for extraction and recovery of the chemical compounds contained in said organic biomass coming from waste.

In the present invention, the term "municipal solid waste or MSW" refers to the solid waste mixing stream comprising predominantly a mixture of municipal and commercial waste. However, the precise composition of MSW varies with the source, and the concentrations and ranges described below must not be taken to be a limitation. Depending on the source, MSW comprise at least one of the following:
- meat waste of any type such as, for example, but not limited to chicken, pork, beef and mutton;
- both used animal and vegetable oils and greases;
- food waste from the fishing industry, ranging from any type of fish to shellfish and their shells;
- agricultural waste, as well as waste from pruning and gardening;
- fruit and vegetable waste; and
- paper and cardboard.

As a result of the heterogeneity of the organic fraction, different proportions of different chemical compounds can be obtained from these MSW.

In the present invention, "reclamation or recovery" is understood to mean the different physical and chemical processes that are carried out on MSW for obtaining and recovering the chemical compounds contained in said MSW. However, despite the diversity of the compositions of MSW, the same compounds are always obtained, but logically in different proportions depending on the material input into the sanitizing and biological thermal stabilization unit. The ranges for obtaining the reclamation compounds in a percentage by weight are the following:
- Fatty acids: [9-20]% (Triglycerides)
- Lactic acid [20-40]%
- Potassium laevulate [20-45]%
- Saccharides [5-20]% (fructose, glucose and sucrose)
- Amino acids [1-5]% (in the largest proportion arginine, alanine, glutamic acid, valine, tryptophan and phenylalanine.)

A first aspect of the present invention relates to a method for municipal solid waste reclamation, characterized in that it comprises the following steps:
- (a) pre-treating the municipal solid waste by the method selected from screening, optical sorter, eddy current separator, magnetic separators, ballistic separators, film separators, sorting, shredder and any combination thereof, and separating the organic fraction resulting from said pre-treatment having an average particle size of between 2 mm and 8 mm;
- (b) performing hydrolysis on the organic fraction obtained in step (a) to decompose the organic matter having an average particle size of between 2 mm and 8 mm obtained in step (a) and form a biomass comprising a wet organic solid phase and a liquid phase;
- (c) mechanically separating the foreign materials of the biomass obtained in step (b) from the wet organic solid phase, which is preferably performed in a separating trommel.

In the present invention "foreign materials" are understood as those materials which are not susceptible to being recovered in terms of materials or energy, comprising plastics, glass, plate glass, bones, rubble comprising but not limited to
- soils and aggregates
- concrete waste
- asphalt pavement waste
- refractory materials
- bricks
- plasters
- wood
- metal or
- blinds.

An advantage of the method is that in step (a) decomposition, not degradation, occurs, given that this decomposition allows chemical molecules of industrial interest to be recovered. Degradation is defined as the chemical process that modifies the composition of a material. This modification entails the deterioration of chemical properties, thereby losing a high organic matter content, yielding humic acids (HA) and fulvic acids (FA) as final products. Other techniques for the treatment of organic matter degrade said matter, impeding the recovery of chemical molecules with a high added value. Chemical decomposition is identified with the cleaving of molecules in a method that gives rise to other molecules of the same nature, but of a shorter length.

This particular feature of the process allows the use of compounds contained in the organic matter for a number of uses, unlike complete degradation, which only allows the recovery of fulvic and humic acids.

Another advantage of the method is that the biomass obtained in step (c) is susceptible to being used for obtaining biofuels.

Additionally, another advantage is that this biomass obtained after said step (c) is free of pathogenic agents and has excellent organic characteristics for the material reclamation thereof.

In a preferred embodiment of the method, the hydrolysis of step (b) is a pressurized thermal hydrolysis. In a more preferred embodiment, the pressurized thermal hydrolysis is performed by introducing the organic fraction of step (a) in an autoclave and introducing steam at a temperature of between 100° C. and 150° C., and with a pressure of between 1.5 bar and 4 bar. More preferably a temperature of between 130° C. and 140° C., and with a pressure of between 1.8 bar and 2.5 bar.

Under these conditions, 4 T/h of wet biomass are obtained for every 6 T/h of MSW that enters.

The advantages of the pressurized thermal hydrolysis technique include:
- It homogenizes the organic fraction.
- It sanitizes said matter.
- It thermally and biologically stabilizes the organic matter.
- It denatures the proteins instead of completely hydrolyzing them. This allows the recovery of specific amino acids at will as a result of the use of specific enzymes.
- It monomerizes polysaccharides, their extraction being much more effective.
- It condenses bulkier triglycerides and eliminates those that are most lightweight, mainly three fatty acids being obtained: oleic acid, palmitic acid and stearic acid.
- It decomposes organic matter, leaving the foreign materials ready to be separated by sizes or densities.

In another preferred embodiment of the method of the present invention, it further comprises the following steps:
- (d) drying the wet organic solid phase obtained in step (c), preferably by means of an industrial drying device; and
- (e) separating the dry organic solid phase obtained in step (d) from the remaining foreign materials by a method selected from densimetry, flip-flop, densimetry, elastic mesh screening and any combination thereof.

In another preferred embodiment of the method of the present invention, it further comprises the steps of
- (f) solid-liquid extraction of dry organic solid phase obtained in step (e) with a non-polar solvent by continuously heating the solvent under reflux to a temperature of at least the evaporation temperature of the selected solvent and 1 bar of pressure, to obtain a liquid fraction and a solid fraction; and
- (g) separating the solvent from the liquid fraction obtained in (f) to obtain a first reclaimed fraction, preferably by distillation.

In a more preferred embodiment of the method of the present invention, the non-polar solvent is selected from heptane, hexane, pentane, cyclohexane, methylcyclohexane and any combination thereof.

In another preferred embodiment of the method of the present invention, the reclaimed liquid fraction obtained in step (g) is transesterified. Said transesterification is performed in order to obtain fatty acids and glycerol.

In another preferred embodiment of the method of the present invention, it further comprises the steps of
(h) drying the solid fraction obtained in step (f);
(i) performing a solid-liquid extraction of the dry solid waste obtained in step
(h) with a solvent by continuously heating said solvent under reflux to at least the evaporation temperature of the selected solvent and 1 bar of pressure, to obtain a liquid fraction and a solid fraction; and
(j) separating the solvent from the liquid fraction obtained in (i).

The solvent used in step (i) will be a more polar solvent than the one used in step (f).

The advantage of step (j) is obtaining a reclaimed liquid fraction of polyhydroxylated compounds having up to 6 carbon atoms, such as: glycerol, butanediol, hexanetriol, hexadiol, pentanol, pentanediol, pentanetriol and mixtures thereof.

In a more preferred embodiment of the method of the present invention, the solvent of step (i) is selected from ethanol, propanol, isopropanol, butanol, 1,3-propanetriol, 1,2-propanediol, 1,2,3-propanetriol and any combination thereof.

In another preferred embodiment of the method of the present invention, it further comprises the steps of
(k) drying the solid fraction obtained in step (f) or (i);
(l) performing a solid-liquid extraction of the solid waste obtained in step (k) with a polar solvent by continuously heating said solvent under reflux to at least the evaporation temperature of the selected solvent and 1 bar of pressure, to obtain a liquid fraction and a solid fraction; and
(m) separating the solvent from the liquid fraction obtained in (l) and drying.

The advantage of step (l) is obtaining a reclaimed fraction of an amino acid buffer, wherein said amino acids recovered are lysine, glycine, serine, histidine, aspartic acid, asparagine, arginine, alanine, glutamic acid, threonine, trans-4-hydroxyproline, proline, valine, methionine, isoleucine, leucine, phenylalanine or tryptophan.

In a more preferred embodiment of the method of the present invention, the solvent of step (l) is water.

In another preferred embodiment of the method of the present invention, it further comprises the following steps:
(n) drying the solid waste obtained in step (l), and
(o) performing acid hydrolysis on the dry solid waste obtained in step (n).

In a more preferred embodiment of the method of the present invention, it further comprises the following steps
(p) neutralizing, preferably with KOH, the product obtained in step (o) to pH 7,
(q) filtering the precipitate obtained in step (p); and
(r) adding a 3:1 mixture of methanol and water onto the crude supernatant remaining in step (q) and drying the obtained product.

The advantage of step (r) is obtaining potassium laevulate.

In another more preferred embodiment of the method of the present invention, it further comprises the following step
(p') distilling the product obtained in step (o) and drying.

The advantage of step (p') is obtaining levulinic acid.

In another preferred embodiment of the method of the present invention, the steps of extraction (l), (i) and/or (f) are performed in a solid-liquid extractor selected from a Soxhlet extractor, extractor using percolation, extractor using immersion, extractor using diffusion, stirred-tank reactors using infusion and an extractor with distillation.

In another preferred embodiment of the method of the present invention, the drying of steps (h), (k) and (n) is performed by a drying device selected from an oven, desolventizer and dryer, desolventizer, toaster, electric oven, rotavapor, desiccating agents, vacuum desiccators, vacuum ovens, silica gel and any combination thereof.

In another preferred embodiment of the method of the present invention, it comprises a step of taking out of the extractor the liquid fraction obtained in steps (l), (i) and/or (f) by pumping by means of an extraction pump and subsequently conducting it to the separation of the solvent and reclaimed fraction.

In another preferred embodiment of the method of the present invention, the separation of the solvent from the liquid fraction of steps (g), (j) and/or (m) is performed in a separator device selected from a skimmer, at least a solvent evaporator, a liquid-solid industrial separator, demoysin separators, FAN separators, centrifugal separators, vertical separators and any combination thereof, for obtaining the reclaimed fraction and the solvent.

In a more preferred embodiment of the method of the present invention, it additionally comprises, after each separation of the solvent from the liquid fraction, a step of desorption performed in a device selected from a solvent stripper, demoysin separators, FAN separators, centrifugal separators, vertical separators, thermal desorber and any combination thereof for the recovery of the reclaimed fraction and solvent which is introduced back into respective steps of extraction (f), (i) or (l).

In another preferred embodiment of the method of the present invention, wherein after each solid-liquid extraction of steps (l), (i) and/or (f), it further comprises a step of conducting the steam generated in the extractor and subsequent separation of the fraction comprising the solvent in liquid state.

In a more preferred embodiment of the method of the present invention, it further comprises after each separation of the fraction comprising the solvent in liquid state, described in the preceding embodiment, a step of separation of the solvent obtained in a separator device selected from a skimmer, at least a solvent evaporator, a liquid-solid industrial separator, demoysin separators, FAN separators, centrifugal separators, vertical separators and any combination thereof, for obtaining the reclaimed fraction and the solvent, for obtaining the reclaimed fraction and the solvent.

In a more preferred embodiment of the method, it comprises a step of recirculation of the separated solvents using recirculation means configured for introducing the solvent separated from each liquid fraction back into said extractor.

Another preferred embodiment of the method of the present invention comprises the following steps
(a) pre-treating the municipal solid waste by the method selected from screening, optical sorter, eddy current separator, magnetic separators, ballistic separators, film separators, sorting, shredder and any combination thereof, and separating the organic fraction resulting from said pre-treatment having an average particle size of between 2 mm and 8 mm;

(b) performing hydrolysis on the organic fraction obtained in step (a) to decompose the organic matter having an average particle size of between 2 mm and 8 mm obtained in step (a) and form a biomass comprising a wet organic solid phase and a liquid phase;

(c) mechanically separating the foreign materials of the biomass obtained in step (b) from the wet organic solid phase and optionally shredding;

(f') solid-liquid extraction of wet organic solid phase obtained in step (c) with a polar solvent by continuously heating the solvent under reflux to at least the evaporation temperature of the selected solvent and 1 bar of pressure, to obtain a liquid fraction and a solid fraction; and (g') separating the solvent from the liquid fraction obtained in (f') to obtain a first reclaimed fraction.

The advantage additionally associated with this embodiment is that the extraction is performed directly, with the subsequent energy savings required for drying the organic phase of the biomass obtained in step (c). Furthermore, the advantage of step (f') is obtaining a reclaimed fraction of polyhydroxylated compounds having up to 6 carbon atoms, such as: glycerol, butanediol, hexanetriol, hexadiol, pentanol, pentanediol, pentanetriol and mixtures thereof.

In more preferred embodiment of the method of the present invention, the solvent of step (f') is water. In an even more preferred embodiment, the reflux temperature will be at least 100° C.

In more preferred embodiment of the method of the present invention, it further comprises the steps of (h') drying the solid fraction obtained in step (f');

(i') performing a solid-liquid extraction of the dry solid waste obtained in step (h') with a non-polar solvent by continuously heating said solvent under reflux to at least the evaporation temperature of the selected solvent and 1 bar of pressure; and (j') separating the solvent from the liquid fraction obtained in (i') and distilling.

In an even more preferred embodiment, the solvent of step (i') is selected from heptane, hexane, pentane, cyclohexane, methylcyclohexane and any combination thereof. In an even more preferred embodiment, the solvent is heptane, and the reflux temperature will be at least 98° C.

Another more preferred embodiment further comprises the following steps:

(k') a subsequent step of drying the solid waste obtained in step (i'), (l') performing acid hydrolysis on the dry solid waste obtained in step (k'), preferably at a pH equal to 1 and with HCl at a concentration between 2 M and 4 M.

The advantage of step (l') is obtaining lactic acid.

In a more preferred embodiment of the method of the present invention, it further comprises the following steps:

(m') neutralizing, preferably with KOH, the product obtained in step (l') to pH 7, (n') filtering the precipitate obtained in step (m'); and (o') adding a 3:1 mixture of methanol and water onto the crude product remaining in step (n') and drying.

The advantage of step (o') is obtaining potassium laevulate.

In another more preferred embodiment of the method of the present invention, it further comprises the following step (p') distilling the product obtained in step (l') and drying.

The advantage of step (p') is obtaining levulinic acid.

In another preferred embodiment of the method of the present invention, the steps of extraction (f') and/or (i') are performed in a solid-liquid extractor selected from a Soxhlet extractor, extractor using percolation, extractor using immersion, extractor using diffusion, stirred-tank reactors using infusion and an extractor with distillation.

In another preferred embodiment of the method of the present invention, the drying of steps (h') and/or (k') is performed by means of a drying device selected from an oven, desolventizer and dryer, desolventizer, toaster, electric oven, rotavapor, desiccating agents, vacuum desiccators, vacuum ovens, silica gel and any combination thereof.

In another preferred embodiment of the method of the present invention, it comprises a step of taking out of the extractor the liquid fraction obtained in steps (f') and/or (i') by pumping using an extraction pump and subsequently conducting it to the separation of the solvent and reclaimed fraction (steps (g') and/or (j')).

In another preferred embodiment of the method of the present invention, the separation of the solvent from the liquid fraction of steps (g') and (j') is performed in a separator device selected from a solvent evaporator, a liquid-solid industrial separator, demoysin separators, FAN separators, centrifugal separators, vertical separators and any combination thereof, for obtaining the reclaimed fraction and the solvent.

In another preferred embodiment of the method of the present invention, it additionally comprises a step of desorption performed in a device selected from a solvent stripper, industrial solvent recovery units, industrial distillers, azeotropic vacuum distillation and any combination thereof for the recovery of the reclaimed fraction and solvent which is introduced back into the separator device.

In another preferred embodiment of the method of the present invention, each solid-liquid extraction of steps (f') and/or (i') further comprises a step of conducting the steam generated in the extractor to a solvent absorber-desorber configured for the separation of a fraction comprising the solvent in liquid state.

In a more preferred embodiment of the method of the present invention, it further comprises a step of separation of the solvent obtained in a separator device selected from a skimmer, at least a solvent evaporator, a liquid-solid industrial separator, demoysin separators, FAN separators, centrifugal separators, vertical separators and any combination thereof, for obtaining the reclaimed fraction and the solvent.

In a more preferred embodiment of the method, it comprises a step of recirculation of the separated solvents using recirculation means configured for introducing the solvent separated from each liquid fraction back into each extractor.

In another preferred embodiment of the method of the present invention, it comprises the following continuous steps (d") introducing the biomass obtained in step (c) in an industrial digester, comprising anaerobic bacterial microorganisms, and wherein said digester is air-tight and under stirring, preferably performed by a method selected from continuous stirring and gas injection in the lower portion of the digester, maintaining a temperature of between 25° C. and 60° C., a pH of between 7 and 8.5 and an amount of nitrogen of 33 kg for every 2000 kg of biomass;

(e") extracting the digestate obtained in step (d") from inside the digester and performing a separation of the liquid and solid fraction from said digestate, preferably in a decanter;

(f") extracting and cooling the biogas obtained in step (d"), preferably in a heat exchanger, to a temperature of between 5° C. and 10° C.; and (g") filtering the biogas cooled in step (f").

In the present invention, "industrial digester" is understood to mean a reactor comprising bacteria and used for processes of biomethanation, which consists of the decomposition of organic matter in the absence of oxygen (anaerobic) to produce a methane-rich gas, biogas, obtaining as a byproduct a semi-liquid waste very rich in organic matter and nutrients, digestate. The main operating parameters of the digester used in the present invention are described below:

Temperature, operating range is mesophilic 25-40° C., though it can operate under thermophilic conditions between 50-60° C.
pH, operating range is 7-8.5,
C/N ratio, operating range 20:1-30:1.
Hydraulic retention time 15-25 days.
Total solids content (20-30%)
Optimal organic load is 5-15 kg $SV/m^3$.

The anaerobic digestion process is made up of four steps: hydrolysis, acidogenesis, acetogenesis and methanogenesis. During the first step of hydrolysis, the carbohydrates, proteins and lipids present in the organic fraction of the waste are decomposed into simpler molecules that are more accessible to the bacteria. During the acidogenesis and acetogenesis phases, the bacteria produce acetic acid, hydrogen, carbon dioxide and different intermediate components (organic acids, alcohols . . . ) which are subsequently used by the methanogenic bacteria for producing methane. It has been reported that hydrolysis is the step that limits the speed of the anaerobic digestion process, and that the bacteria involved in the methanogenesis phase are more sensitive to the operating conditions and the presence of toxic substances.

The particle size of the organic matter affects the initial phase of hydrolysis. Too large a particle size reduces the efficiency of hydrolysis, reducing biogas production; Too small a particle size promotes the production of organic acids, acidifying the medium, complicating the operation of the digester because the pH is below the optimal value described above.

Nitrogen is required by methanogenic bacteria to obtain proteins during the anaerobic digestion process. A high C/N ratio means that the nitrogen depletes rapidly, so the methanogenic bacteria cannot produce more biogas, reducing biogas production. A low C/N ratio entails a high nitrogen content, which results in the additional formation of ammonia (strong base), causing the values to exceed the optimal operating range.

In the present invention, "biogas" is understood to mean a gas which is primarily made up of methane (50-5% vol.), carbon dioxide (50-35% vol.) and other impurities (the main impurities by amount are $H_2S$, $NH_3$, COVs, and steam), which must be partially or completely removed for subsequent recovery of the biogas.

In the present invention, "digestate" is understood to mean the solid and liquid byproduct resulting from anaerobic digestion, and it has a potential use as an organic fertilizer.

The advantages of the thermal treatment of hydrolysis over the biomethanation process are
it reduces the presence of contaminants and toxic components in the substrate used in the anaerobic digestion process. During the thermal treatment, aldehydes and acid gases (HCl, HF, $SO_2$, $NH_3$) are removed as part of the non-condensables contained in the gas effluent (air) of thermal hydrolysis. This causes a drop in the presence of contaminants of the biogas obtained and in the operating costs associated with post-treatment before the final application of the biogas;
it reduces the presence of disinfectants, pesticides or organic solvents in the biomass used as feedstock for the digester. During thermal treatment, they are removed as condensables dissolved in the liquid effluent coming from the thermal hydrolysis. This prevents introducing contaminants that are toxic for methanogenic bacteria;
it improves the physical properties of the digestate: solid-liquid separation and viscosity. Solid-liquid separation of the digestate is improved, reducing the volume of the solid fraction by 20-40%. This involves a drop in the volume of the solid fraction, reducing the surface area required for the composting process. The digestate presents a lower viscosity, which entails a reduction of costs associated with mixing the substrate in the digester, and the costs associated with driving the digestate after the biomethanation process;
it accelerates the composting process of the digestate, reducing the time required between 20-30%;
it breaks up the organic matter of the municipal solid waste to a particle size between 2-4 mm without the need for a shredding process. This means that during the separation of foreign materials, the organic matter has a small particle size and virtually all foreign materials are removed. Fewer foreign materials are therefore introduced in the digester, improving the operation of the biodigester, and reducing the post-treatment tasks of the digestate/compost. Additionally, by having fewer foreign materials, the substrate can contain more digestible substrate, increasing the specific biogas production per ton treated;
it increases the C/N ratio within optimal values, preventing the additional formation of ammonia, which would entail an increase in pH above the operating values;
it prevents introducing pathogenic agents and other bacteria that may compete with or affect the microbiology of the process;
a substrate with higher density is obtained, so it is more compact and has less occluded air which can negatively affect methanogenic bacteria;
it facilitates the step of hydrolysis of the anaerobic digestion process, so the organisms can more readily access the partially hydrolyzed organic matter. This increases the rate of biogas production between 20-35%, and it increases the specific biogas production per kg of volatile solids between 20-30%. The increase in methane generation increases the cost-effectiveness of the process since the demand of the facility itself is covered, and greater surplus energy is generated.

In a more preferred embodiment of the method, it additionally comprises a step before step (d") and after step (c) of shredding the biomass obtained in step (c) to a particle size of 2 mm and diluting in water to a percentage of moisture content of between 55% and 65%.

Throughout the description and the claims, the word "comprises" and its variants are not intended to exclude other technical features, additives, components or steps. For those skilled in the art, other objects, advantages and features of the invention may be inferred from both the description and the embodiment of the invention. The following examples and figures are provided by way of example and are not intended to limit the present invention.

EXAMPLES

Next, the invention will be illustrated by means of assays carried out by the inventors which clearly shows the industrial viability of the invention.

Example 1

The pre-treatment of the municipal solid waste consists of a series of separation operations the purpose of which is to recover most of the recyclable materials, such as bricks, plastics, ferrous and non-ferrous metals and glass. After said pre-treatment, the waste is further concentrated into the organic fraction and has a particle size suitable for subsequent treatment, by means of pressurized thermal hydrolysis treatment.

Once the organic matter is pre-selected, it is introduced in the autoclave system, which operates by introducing steam (135° C.) under pressure conditions (3 bar) for the purpose of homogenizing, decomposing and sanitizing the municipal solid waste.

Physical and chemical transformations take place in the process with the subsequent decomposition of the organic matter. This decomposition (not degradation) is an important feature of the system, given that this decomposition allows chemical molecules of industrial interest to be recovered. Other techniques for the treatment of organic matter degrade said matter, impeding the recovery of chemical molecules with a high added value.

Once the pressurized thermal hydrolysis process has ended, the wet biomass is treated in a step of post-treatment. At the end of this last process, a biologically and thermally stabilized biomass with an organic matter content greater than 98% is obtained.

This biomass is free of pathogenic agents and has excellent organic characteristics for reclaiming the material.

Example 2

Chemical titration starts with a series of extractions from the obtained biomass of the organic fraction of the municipal solid waste. To that end, Soxhlet extraction equipment and solvents from a lower to higher polarity are used.

Heptane, ethanol and finally water will be used (but they can be other solvents of a similar nature . . . )

Extraction with Hexane:

60 g of MSW biomass are introduced in Soxhlet extraction equipment provided with a coolant, a liter flask and a heating mantle. 600 ml of heptane are introduced in the balloon (B.P. 78 C). The most non-polar compounds of all of them will be extracted with this solvent. Fats. After 24-48 hours under reflux the reaction is stopped.

The solvent is removed in a rotavapor under reduced pressure, obtaining the extract of lipophilic substances, such as fatty acids, mostly palmitic acid C16:0 and oleic acid C18 with a yield of 10% by weight with respect to the initial weight of biomass introduced, that is, for every 100 kg of biomass 10 kg of fatty acids are obtained.

Figure 1:
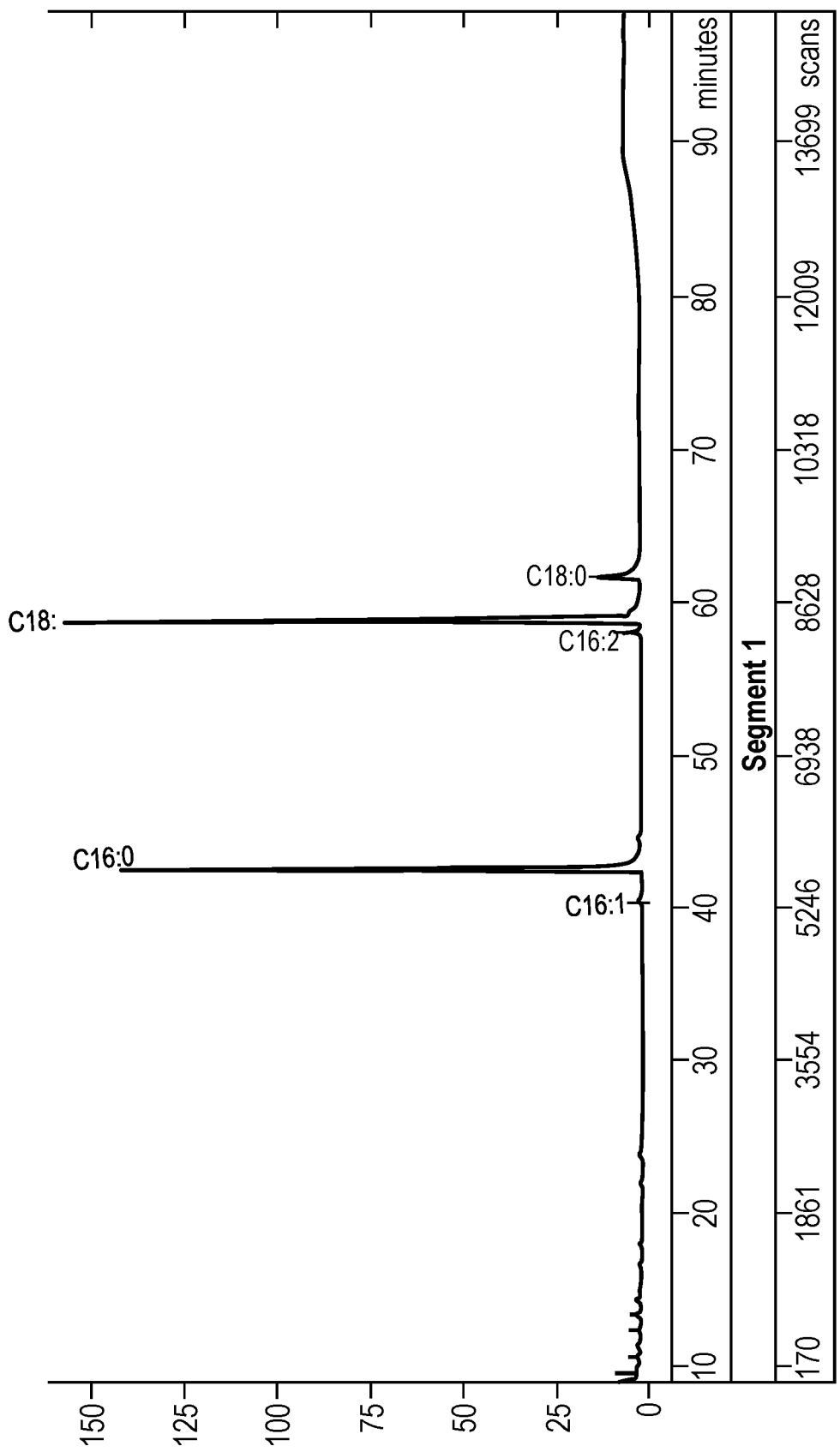
FIG. 1. Chromatogram of fatty acids.

After purification, said extract is characterized by chromatographic assays. In the spectrum, there is identified mostly a triglyceride with a chiral center (FIG. 1).

Said triglyceride is hydrolyzed using hydrochloric acid as a catalyst, obtaining:

fatty acids esters from which biodiesel can be obtained; and glycerol.

Extraction with Ethanol

For this second extraction ethanol is used as solvent (B.P. 78° C.).

With ethanol, polar compounds are extracted, this extraction is performed for the purpose of extracting and characterizing the polyhydroxylated compounds (glycosides).

To that end, following the preceding method, the reaction was left under reflux in a Soxhlet equipment between 12 and 48 hours. The recovery occurred and the reaction was stopped.

The solvent was removed under reduced pressure in a rotavapor (recovered for subsequent extractions), the compounds that are soluble in this solvent are contained in the crude product with a yield of about 10% by weight with respect to the initial weight of biomass introduced, that is, for every 100 kg of biomass 10 kg of fatty acids are obtained.

The $^1$H NMR spectrum of the ethanol extract shows signals characteristic of polyhydroxylated compounds (broad signals between 3 and 6 ppm) characteristic of said compounds.

Extraction with Water

Lastly, to finish this series of extractions, water was used as solvent (B. P. 100° C.), in the Soxhlet extraction equipment. The reaction was left under reflux for 12-36 hours and after that time the solvent was removed in the rotavapor for the purpose of recovering the most polar compounds of all of them (carbohydrates and proteins), with a yield close to 10% by weight with respect to the initial weight of biomass introduced, that is, for every 100 kg of biomass 10 kg of fatty acids are obtained.

An important particular feature of the process of sanitizing MSW is that it does not fragment the proteins, it simple denatures them, which thereby allows the isolation of the amino acids that form the proteins with relative ease.

The characterization of this water extract by $^1$H NMR resonance gives signals characteristic of monomerized proteins and carbohydrates, that is, in the form of monosaccharides.

Next, the amounts obtained from each of the extracts are shown below by way of clarifying summary.

TABLE 1

Tabulated summary of extractions, yields and solvent for NMR

| | Solvent used | Mass obtained in extract (g.) | Percentage | Name NMR (Solvent) |
|---|---|---|---|---|
| Municipal Solid Waste (MSW) mass (g): 60 | Heptane | 5.13 | 9% | AVS-I-16 Heptane (CDCl$_3$) |
| | Methanol | 5.44 | 9% | AVS-I-16 Methanol (MeOD) |
| | Water | 5.66 | 9% | AVS-I-16 (D$_2$O) |
| | Waste: 38.52 g (73%) | | | |

27% is recovered from the biomass with the different extractions, obtaining from these extracts triglycerides, saccharides, polyalcohols, amino acids and proteins.

Example 3

Chemical Treatment of the Solid Waste from the Extraction with Water of Example 2.

73% of the biomass not extracted by the solid-liquid extractions (Soxhlet technique) is treated.

To that end, HCl (4 M) is used. This fraction is hydrolyzed for the purpose of reducing as much as possible the total amount of waste. In this case, HCl acts as catalyst.

With the product obtained from acid hydrolysis, neutralization is performed with K(OH) to pH=7.

KCl salts characteristic of neutralizing an acid and a base precipitate and must be removed by filtration.

A mixture of methanol/water (3:1) is added to the crude product (after removing the salts) for the purpose of purifying same.

Figure 2:
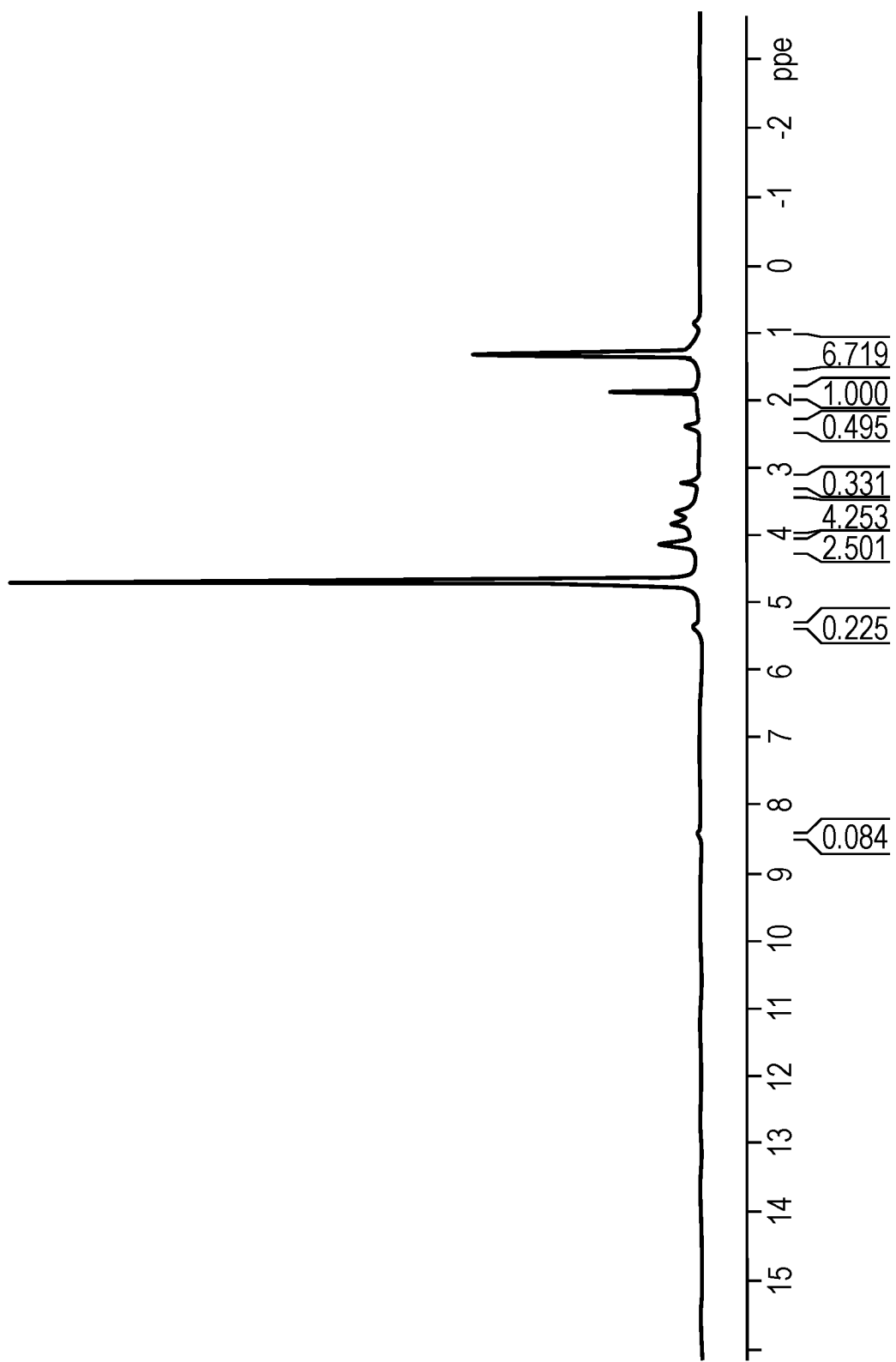
FIG. 2. $^1H$ NMR spectrum of lactic acid.

$^1$H NMR is performed on this crude product (FIG. 2), giving a signal of a main compound, lactic acid.

Example 4

After hydrolysis on the waste not extracted from the heptane fraction, the sample is distilled with a simple distillation equipment for the purpose of removing excess HCl coming from hydrolysis. The formation of KCl salts is thereby prevented.

Figure 3:
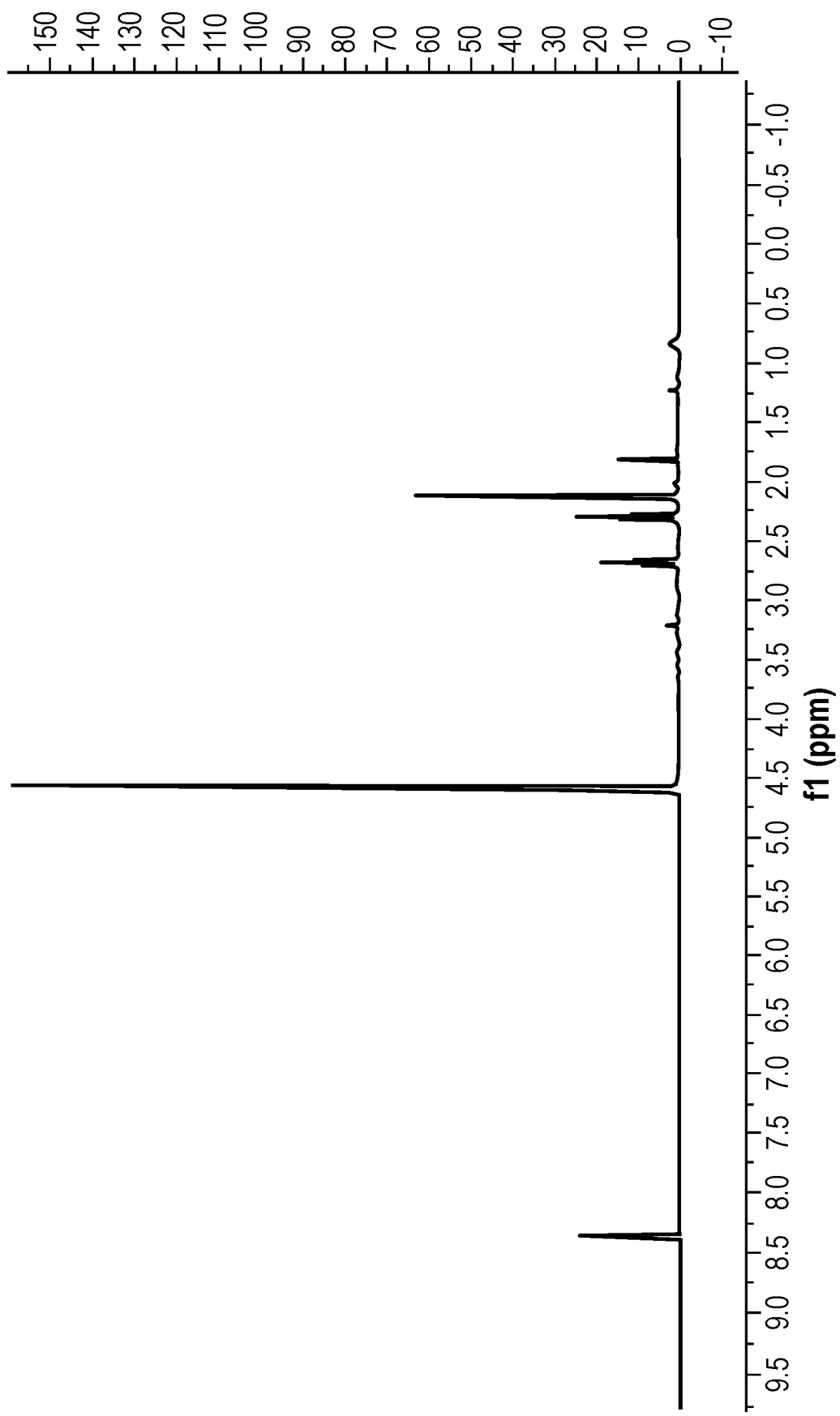
FIG. 3. $^1$H NMR spectrum of levulinic acid.

A dark colored oil is obtained, which is characterized by magnetic resonance:

The shifts are seen in the spectrum (FIG. 3)
1—CCH3-CO: 2.1 ppm
2—HOOC—CH2: 2.5 ppm
3—O—CH3: 2.69 ppm
Signals Characteristic of Levulinic Acid
In addition to $^1$H NMR (FIG. 3) similar assays, $^{13}$C-NMR and HBMC are performed.

The presence of said acid is confirmed.

Example 5

Example of a wet industrial extraction process and subsequent hydrolysis of the biomass obtained from the organic fraction of municipal solid waste.

The process described in Example 5 starts after Example 1, that is, with the biomass at the outlet of the trommel after thermal hydrolysis.

The wet biomass, at the outlet of the trommel, can be subjected to a subsequent step of shredding or grinding to favor subsequent contact between the phases in the industrial extractor system.

Once the shredding process ends (if needed), the components contained in the biomass are extracted.

To that end:

The wet biomass is introduced continuously through a feeding hopper (1) in an industrial extractor (2) (as an example, extraction equipment using percolation or immersion could be used). Water is used as solvent. The purpose of this first operation is to utilize the lactic acid content of the biomass.

Once the extraction process with water has ended, the organic fraction with solvent (21) is sent through a desolventizer/dryer (3), in said desolventizer/dryer hot air is introduced at one of the intermediate levels and cold air is introduced at the lower level. The solvent in vapor state is thereby removed from said organic fraction and is taken to a solvent absorber/desorber (5), where the extraction and drying vapors are cleaned by industrial steam injection (26), whereas the organic fraction without solvent (24) is obtained from said desolventizer/dryer (3). Furthermore, the system, has a solvent evaporator with a stripper (4), also with industrial steam injection (25) for obtaining the product to be reclaimed with the lowest possible solvent fraction, and also recovering the solvent used which, together with that obtained in the solvent absorber/desorber (5), is reused in the extraction process again, thereby preventing excessive solvent cost.

Lastly, said product obtained from the solvent evaporator with stripper (4) and from the solvent absorber/desorber (5) is separated from the solvent in a solid-liquid separator (6) used for such purpose, thus obtaining the reclaimed product free of solvents (27), and where the solvent can be recirculated in the extractor (2).

The dry biomass (24) is sent through a similar system.

The biomass resulting from the prior process feeds a second extractor (8) through a feeding hopper (7). This time heptane is used as a solvent.

The purpose is to recover the fatty acids contained in the biomass for the subsequent recovery thereof. Once the biomass is free of said acids, the method followed is the same as in the preceding case, that is, recovery of the solvent with the desolventizer/dryer (9), purification thereof in a solvent evaporator with stripper (10), recirculation back into the system with a solvent absorber/desorber (11) with the steam injections (35 and 36) and, lastly, the liquid-liquid separation (12) for obtaining the reclaimed product from this extraction (37), which are fatty acids and glycerol characteristic of this extraction.

Once the series of extractions ends, the biomass cleaned of fatty acids and lactic acid (34) is taken to an industrial reactor to start acid hydrolysis of the organic matter. As an example, an industrial glass-lined batch reactor with a 2-ton capacity in each unit will be used. In this point, 4 M HCl is added to acidity pH=1 and is then neutralized with an Na(OH) or K(OH) type strong base (chosen due to their availability and price).

Once the hydrolysis ends, the precipitate is collected. The obtained product is Na or K laevulate (depending on the base used for neutralizing). The amino acids are in the aqueous fraction.

Said amino acids are purified by fractional distillation for subsequent recovery.

Industrial yields starting from 2000 kg of material are:
1—Lactic acid: 20%→400 Kg
2—Levulinic acid: 40%→800 kg
3—Fatty acids: 8%→160 Kg
4—Amino acids: 3%→60 Kg
That is, 1420 kg are recovered out of an initial 2000 kg.

Example 6

Figure 4:
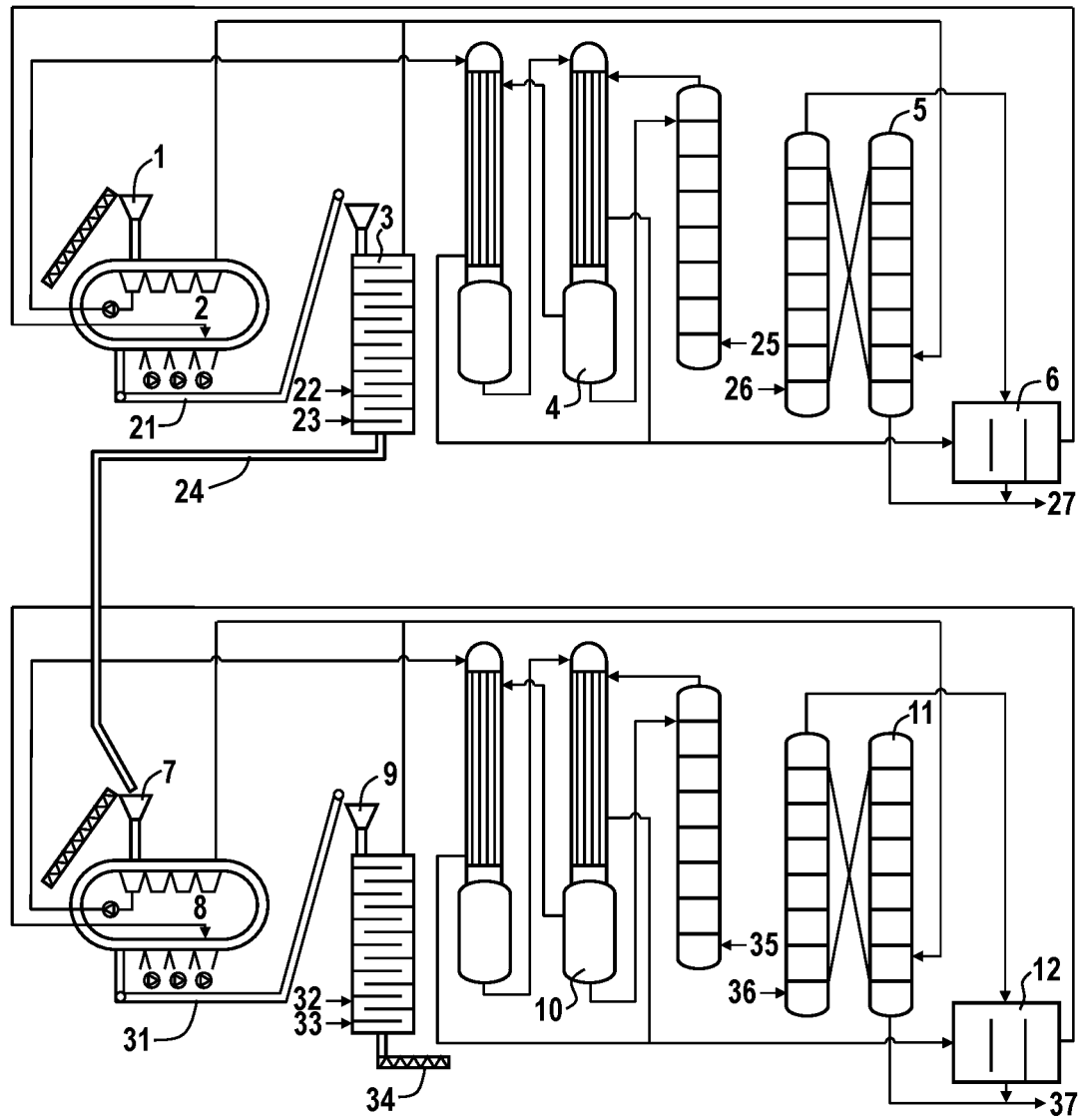
FIG. 4. Diagram showing the flow of the wet industrial method.

The industrial process described in this Example 6 (FIG. 4) starts after Example 1, that is, it starts with the biomass output obtained at the outlet of the trommel of the pressurized thermal hydrolysis process.

The wet biomass, at the outlet of the trommel, may be subjected to a shredding process if needed to assure optimal particle size of 2 mm. Additionally, the biomass can be diluted with water to adjust the total solids content.

The wet biomass is fed continuously by a conveyor belt into the industrial digester (a complete-mix digester). The digester is completely sealed against the entrance of air and incorporates a heating system to keep the temperature of the process at 35° C. The wet biomass is mixed as a result of the continuous mechanical action of a stirrer, facilitating contact between the organic matter and the bacteria. The organic matter is initially hydrolyzed, and subsequently degraded, producing biogas as a final product. The material digested by the bacteria, the digestate, is pumped out of the digester.

The obtained biogas is saturated at a temperature of 35° C. and contains impurities (mainly $H_2S$) that must be removed before utilization in combined cycles. First, the dew point of the biogas is reduced to 5° C. in a heat exchanger to reduce the water content. Subsequently, the biogas is subjected to a filtration process in an activated carbon filter to remove $H_2S$. The biogas is introduced in a combined cycle unit, in which electricity and heat are produced with efficiencies between 40% and 60%. The heat is used for operation of the biomethanation plant. The electricity is used for internal consumption and should any be left over, it can be dumped into the grid.

The digestate is subjected to a separation process (as an example, a decanter could be used) for separating the liquid fraction from the solid fraction. The liquid fraction can be recirculated into the digester or used directly as irrigation water. The solid fraction is subject to a composting process for a period of 1 week.

Industrial yields starting from 2000 kg of material are:
1. Biogas=180 $Nm^3/h$
2. Digestate=950 kg/h

The invention claimed is:

1. A method for municipal solid waste reclamation, comprising the following steps:
    (a) pre-treating the municipal solid waste by screening, optical sorter, eddy current separator, magnetic separators, ballistic separators, film separators, sorting, shredder or any combination thereof, and separating a organic fraction resulting from said pre-treatment having an average particle size of between 2 mm and 8 mm;
    (b) performing pressurized thermal hydrolysis at a temperature of between 100° C. and 150° C., and with a pressure of between 1.5 bar and 4 bar on the organic fraction obtained in step (a) to decompose a organic matter having an average particle size of between 2 mm and 8 mm and form a biomass comprising a wet organic solid phase in turn comprising foreign materials and a liquid phase; and
    (c) mechanically separating the foreign materials from the wet organic solid phase obtained in step (b).

2. The method for municipal solid waste reclamation according to claim 1, wherein the hydrolysis of step (b) is pressurized thermal hydrolysis occurring in an autoclave and introducing steam at the temperature of between 100° C. and 150° C.

3. The method for municipal solid waste reclamation according to claim 2, wherein steam is introduced in the autoclave at a temperature of between 130° C. and 140° C., and with a pressure of between 1.8 bar and 2.5 bar.

4. The method for municipal solid waste reclamation according to claim 1, further comprising the following steps:
    (d) drying the wet organic solid phase obtained in step (c); and
    (e) separating the dry organic solid phase obtained in step (d) from the remaining foreign materials by a method selected from densimetry, flip-flop, densimetry, elastic mesh screening and any combination thereof;
    (f) performing solid-liquid extraction of dry organic solid phase obtained in step (e) with a non-polar solvent by continuously heating the solvent under reflux to a temperature of at least a evaporation temperature of the non-polar solvent and 1 bar of pressure, to obtain a liquid fraction and a solid fraction; and
    (g) separating the solvent from the liquid fraction obtained in (f) to obtain a first reclaimed fraction, wherein the liquid fraction obtained in step (g) is transesterified, wherein the non-polar solvent is selected from heptane, hexane, pentane, cyclohexane, methylcyclohexane and any combination thereof comprising the steps of:
    (h) drying the solid fraction obtained in step (f);
    (i) performing a solid-liquid extraction of a dry solid waste obtained in step (h) with a solvent by continuously heating said solvent under reflux, to obtain a liquid fraction and a solid fraction, wherein the solvent used in step (i) will be a more polar solvent than the one used in step (f); and
    (j) separating the solvent from the liquid fraction obtained in (i) to obtain a reclaimed fraction, wherein the solvent of step (i) is selected from ethanol, propanol, isopropanol, butanol, 1,3-propanetriol, 1,2-propanediol, 1,2,3-propanetriol and any combination thereof comprising the steps of:
    (k) drying the solid fraction obtained in step (f) or (i);
    (l) performing solid-liquid extraction of a dry solid waste obtained in step (k) with a polar solvent by continuously heating said solvent under reflux, to obtain a liquid fraction and a solid fraction; and
    (m) separating the solvent from the liquid fraction obtained in (l) for obtaining a reclaimed fraction; and wherein the polar solvent of step (l) is water.

5. The method for municipal solid waste reclamation according to claim 4, further comprising the following steps:
    (n) drying the solid fraction obtained in step (l), and
    (o) performing acid hydrolysis on a dry solid waste obtained in step (n).

6. The method for municipal solid waste reclamation according to claim 5, further comprising the following steps:
    (p) neutralizing a product obtained in step (o) to pH 7;
    (q) filtering the precipitate obtained in step (p); and
    (r) adding a 3:1 mixture of methanol and water onto the supernatant remaining in step
    (q) and drying a obtained product.

7. The method for municipal solid waste reclamation according to claim 5, further comprising the following step:
    (p') distilling the product obtained in step (o) and drying.

8. The method for municipal solid waste reclamation according to claim 4, wherein the steps of extraction (f), (i) and/or (l) are performed in a solid-liquid extractor selected from a Soxhlet extractor, extractor using percolation, extractor using immersion, extractor using diffusion, stirred-tank reactors using infusion and an extractor with distillation.

9. The method for municipal solid waste reclamation according to claim 5, wherein the drying of steps (h), (k) and/or (n) is performed by means of a drying device selected from an oven, desolventizer and dryer, desolventizer and toaster, electric oven, rotavapor, desiccating agents, vacuum desiccators, vacuum ovens, silica gel and any combination thereof.

10. The method for municipal solid waste reclamation according to claim 4, wherein the separation of the solvent from the liquid fraction of steps (g), (j) and/or (m) is performed in a separator device selected from a skimmer, at least a solvent evaporator, a liquid-solid industrial separator, demoysin separators, FAN separators, centrifugal separators, vertical separators and any combination thereof, for obtaining the reclaimed fraction and the solvent;
    and further comprising, after each separation of the solvent from the liquid fraction, a step of desorption performed in a device selected from a solvent stripper, demoysin separators, FAN separators, centrifugal separators, vertical separators, thermal desorber and any combination thereof for the recovery of the reclaimed fraction and solvent.

11. The method for municipal solid waste reclamation according to claim 4, wherein after each solid-liquid extraction of steps (l), (i) and/or (f), it further comprises comprising a step of conducting a steam generated in a extractor and subsequent separation of the fraction comprising the solvent in liquid state;
and further comprising after each separation of the liquid fraction comprising the solvent in liquid state a step of separation of the solvent obtained in a separator device selected from a skimmer, at least a solvent evaporator, a liquid-solid industrial separator, demoysin separators, FAN separators, centrifugal separators, vertical separators and any combination thereof, for obtaining the reclaimed fraction and the solvent.

12. The method for municipal solid waste reclamation according to claim 4, comprising a step of recirculation of the separated solvents wherein the solvent separated from each liquid fraction are introduced back into the corresponding steps of extraction (f), (i) or (l).

13. The method for municipal solid waste reclamation according to claim 1, comprising the following steps of:
(f') solid-liquid extraction of wet organic solid phase obtained in step (c) with a polar solvent by continuously heating the solvent under reflux to a temperature of at least 100° C. and 1 bar of pressure, to obtain a liquid fraction and a solid fraction; and
(g') separating the solvent from the liquid fraction obtained in (f') to obtain a first reclaimed fraction; and wherein the solvent is water.

14. The method for municipal solid waste reclamation according to claim 13, comprising the following steps of:
(h') drying the solid fraction obtained in step (f');
(i') performing a solid-liquid extraction of a dry solid waste obtained in step (h') with a non-polar solvent by continuously heating said solvent under reflux to a temperature of at least 98° C. and 1 bar of pressure, to obtain a liquid fraction and a solid fraction; and
(j') separating the solvent from the liquid fraction obtained in (i') and distilling; and wherein the non-polar solvent is selected from heptane, hexane, pentane, cyclohexane, methylcyclohexane and any combination thereof and wherein it further comprises the following steps:
(k') drying a solid waste obtained in step (i'),
(l') performing acid hydrolysis on a dry solid waste obtained in step (k');
and further comprising the following steps:
(m') neutralizing, a product obtained in step (l') to pH 7,
(n') filtering a precipitate obtained in step (m'); and
(o') adding a 3:1 mixture of methanol and water onto a crude product remaining in step (n') and drying; and
(p') distilling a product obtained in step (o') and drying.

15. The method for municipal solid waste reclamation according to claim 14, wherein the steps of extraction (f') and/or (i') are performed in a solid-liquid extractor selected from a Soxhlet extractor, extractor using percolation, extractor using immersion, extractor using diffusion, stirred-tank reactors using infusion and an extractor with distillation, wherein the drying of steps (h') and/or (k') are performed by a drying device selected from an oven, desolventizer and dryer, desolventizer, toaster, electric oven, rotavapor, desiccating agents, vacuum desiccators, vacuum ovens, silica gel and any combination thereof, wherein pumping the liquid fraction obtained in steps of extraction (f') and/or (i') by an extraction pump and subsequently conducting the liquid fraction to the steps of the separation of the solvent and reclaimed fraction, wherein the separation of the solvent from the liquid fraction of steps (g') and (j') are performed in a separator device selected from a solvent evaporator, a liquid-solid industrial separator, demoysin separators, FAN separators, centrifugal separators, vertical separators and any combination thereof, for obtaining the reclaimed fraction and the solvent, further comprising, after each separation of the solvent from the liquid fraction, a step of desorption performed in a device selected from a solvent stripper, demoysin separators, FAN separators, centrifugal separators, vertical separators, thermal desorber and any combination thereof for the recovery of the reclaimed fraction and solvent which is introduced back into the separator device.

16. The method for municipal solid waste reclamation according to claim 14, wherein each solid-liquid extraction of steps (f') and/or (i') further comprising a step of conducting the steam generated in the extractor followed by a step of separation of a fraction comprising the solvent in liquid state further comprising a step of separation of the solvent obtained in a separator device selected from a skimmer, at least a solvent evaporator, a liquid-solid industrial separator, demoysin separators, FAN separators, centrifugal separators, vertical separators and any combination thereof, for obtaining the reclaimed fraction and the solvent.

17. The method for municipal solid waste reclamation according to claim 15, further comprising a step of recirculation of the separated solvents followed by a step of introduction of the solvent separated from each liquid fraction back into the corresponding steps of extraction (f') and/or (i').

18. The method for municipal solid waste reclamation according to claim 1, further comprising the following continuous steps
(d") introducing a biomass obtained in step (c) in an industrial digester, comprising anaerobic bacterial microorganisms, and wherein said digester is air-tight and under continuous stirring, maintaining a temperature of between 25° C. and 60° C., a pH of between 7 and 8.5 and an amount of nitrogen of 33 kg for every 2000 kg of biomass;
(e") extracting the digestate obtained in step (d") from inside the digester and performing a separation of a liquid and solid fraction from said digestate;
(f") extracting and cooling a biogas obtained in step (d"), to a temperature of between 5° C. and 10° C.; and
(g") filtering the biogas cooled in step (f").

19. The method for municipal solid waste reclamation according to claim 18, further comprising a step, before step (d") and after step (c), of shredding the biomass obtained in step (c) to a particle size of 2 mm and diluting in water to a percentage of moisture content of between 55% and 65%.

* * * * *